US009856506B2

(12) United States Patent
Hosaka et al.

(10) Patent No.: US 9,856,506 B2
(45) Date of Patent: Jan. 2, 2018

(54) METHOD FOR EXAMINING MICROORGANISMS

(71) Applicant: SATAKE CORPORATION, Tokyo (JP)

(72) Inventors: Yukio Hosaka, Hiroshima (JP); Shinya Fushida, Hiroshima (JP); Akiko Nakata, Hiroshima (JP); Kazuhiko Koike, Hiroshima (JP)

(73) Assignee: SATAKE CORPORATION, Tokyo (JP)

( * ) Notice: Subject to any disclaimer, the term of this patent is extended or adjusted under 35 U.S.C. 154(b) by 0 days.

(21) Appl. No.: 14/894,492

(22) PCT Filed: May 16, 2014

(86) PCT No.: PCT/JP2014/063113
§ 371 (c)(1),
(2) Date: Nov. 27, 2015

(87) PCT Pub. No.: WO2014/192565
PCT Pub. Date: Dec. 4, 2014

(65) Prior Publication Data
US 2016/0122796 A1 May 5, 2016

(30) Foreign Application Priority Data
May 29, 2013 (JP) .................................. 2013-112978

(51) Int. Cl.
C12Q 1/02 (2006.01)
C12Q 1/06 (2006.01)
(Continued)

(52) U.S. Cl.
CPC ................. C12Q 1/06 (2013.01); C12Q 1/02 (2013.01); G01N 1/30 (2013.01); G01N 21/6428 (2013.01);
(Continued)

(58) Field of Classification Search
CPC ........ C12Q 1/06; G01N 1/30; G01N 21/6428; G01N 2001/302; G01N 2021/6439; G01N 2201/062
See application file for complete search history.

(56) References Cited

U.S. PATENT DOCUMENTS

2009/0093045 A1  4/2009 Takenaka et al.
2015/0219548 A1  8/2015 Nakata et al.

FOREIGN PATENT DOCUMENTS

EP  0653492 A2   5/1995
JP  H03-244395 A  10/1991
(Continued)

OTHER PUBLICATIONS

Ruiz, GM et al, "Global spread of microorganisms by ships: Ballast water discharged from vessels harbours a cocktail of potential pathogens" Nature, Nov. 2, 2000, 408, pp. 49-50. doi:10.1038/35040695.*

(Continued)

Primary Examiner — Chris R Tate
Assistant Examiner — Aaron J Kosar
(74) Attorney, Agent, or Firm — Orion Consulting, Ltd.; Joseph P. Farrar, Esq.

(57) ABSTRACT

A method for examining microorganisms has a sampling preparation step including a fluorescence staining step of stirring and mixing certain amounts of a sample and a fluorescence staining reagent, a still standing step of leaving the solution after the fluorescence staining step to still stand for a certain time, and a dilution step of diluting the solution after the still standing step with a liquid that emits no fluorescence.

2 Claims, 6 Drawing Sheets

(51) Int. Cl.
*G01N 21/64* (2006.01)
*G01N 33/58* (2006.01)
*G01N 1/30* (2006.01)

(52) U.S. Cl.
CPC ..... *G01N 33/582* (2013.01); *G01N 2001/302* (2013.01); *G01N 2021/6439* (2013.01); *G01N 2201/062* (2013.01)

(56) References Cited

FOREIGN PATENT DOCUMENTS

| | | | |
|---|---|---|---|
| JP | 2004187534 A | 7/2004 | |
| JP | 2007135582 A | 6/2007 | |
| JP | 2008054509 A | 3/2008 | |
| JP | 2009085898 A | 4/2009 | |
| JP | 2014042463 A | 3/2014 | |
| WO | 2014030729 A1 | 2/2014 | |

OTHER PUBLICATIONS

Murphy, KR et al "Optimized Parameters for Fluorescence-Based Verification of Ballast Water Exchange by Ships" Environ. Sci. Technol., Feb. 24, 2006, 40 (7), pp. 2357-2362. DOI: 10.1021/es0519381.*

PR Jackson, MG Pappas and BD Hansen "Fluorogenic Substrate Detection of Viable Intracellular and Extraceliular Pathogenic Protozoa" Science, 1985, 227(4685),435-438. DOI: 10.1126/science.257822.*

Welschmeyer et al., "A portable, sensitive plankton viability assay for IMO shipboard ballast water compliance testing," Proceedings of the IMO Globallast Conference: Compliance Monitoring and Enforcement, Oct. 2011, pp. 127-139, Istanbul, Turkey.

Alsharif, et al., "Application Note: Bacterial Detection and Live/Dead Discrimination by Flow Cytometry," BD Biosciences, Apr. 2002, pp. 1-6, San Jose, California.

Givan, A.L., "Critical Aspects of Staining for Flow Cytometry," chapter in In Living Color: Protocols in Flow Cytometry and Cell Sorting (R. Diamond and S. DeMaggio, eds), 2000, pp. 142-164, Springer, Berlin.

International Search Report and Written Opinion for Application No. PCT/JP2014/063113 dated Aug. 19, 2014.

Taiwanese Office Action for Application No. 103118688 dated Jul. 14, 2017 , 11 pages.

Hsiu-Jung Yuan, "Purification and characterization of β-glucosidase from Poenibacillus polymyxa Bs83", Institute of Biochemical Sciences and Technology, Chaoyang University of Technology, Thesis for the Degree of Master, Jun. 22, 2011(Oct. 28, 2010), pp. 22-23, Section 3-18 "Total Protein Analysis."

* cited by examiner

FIG. 5
(a)
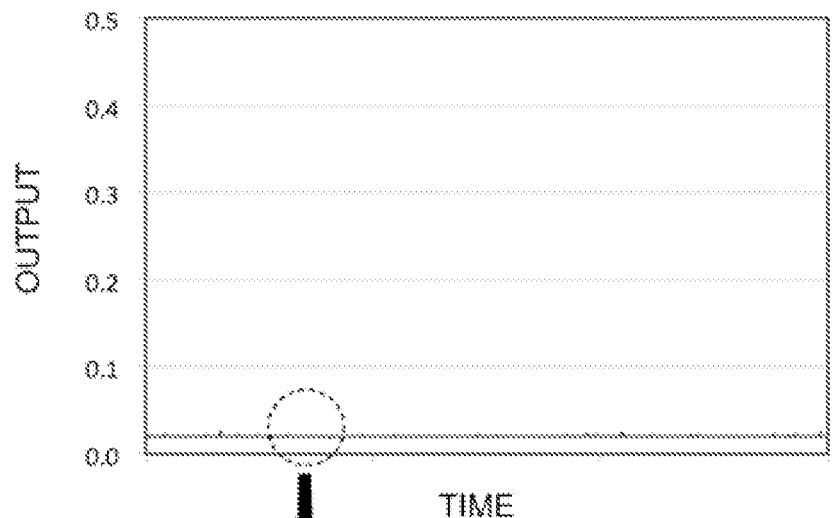
(b)
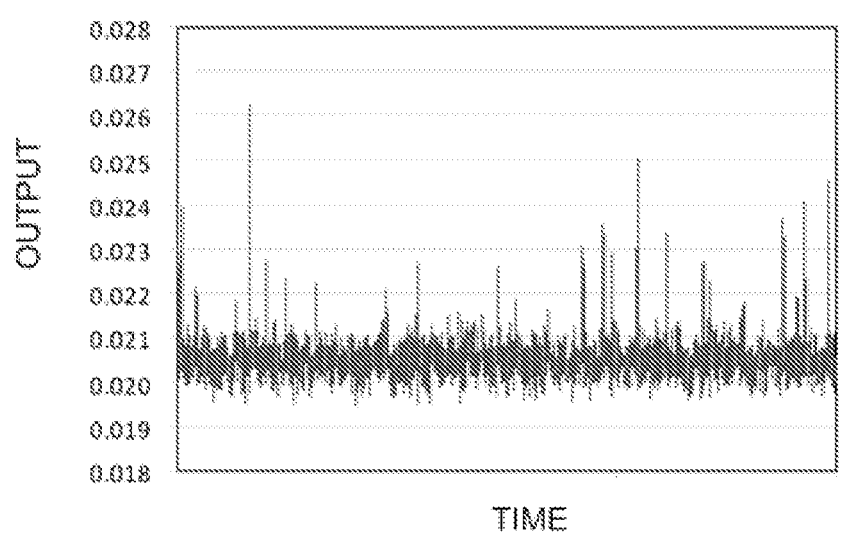

METHOD FOR EXAMINING MICROORGANISMS

BACKGROUND

Technical Field

The present invention relates to a method for examining microorganisms, and in particular, relates to a method for examining microorganisms, the method being suitable for detecting microorganisms such as planktons that are included and live in ballast water or the like.

Background Art

A ship carrying no cargoes is loaded with ballast water in order to stabilize the ship when it sails, and discharges the ballast water in a marine area where cargoes are carried on the ship.

The ballast water is usually discharged in a marine area different from the marine area where the ballast water is loaded on the ship, and therefore, the following problem may be caused: microorganisms such as planktons and bacteria included in the ballast water are transported to a marine area other than the native habitats thereof to disrupt ecosystem.

In order to address such a problem, international rules for the regulation of ballast water have been established, and "the International Convention for the Control and Management of Ships' Ballast Water and Sediments (Ballast Water Management Convention)" has been adopted.

In the "Guidelines for Ballast Water Sampling (G2)" related to the above Ballast Water Management Convention, "Ballast Water Discharge Standards (D-2)" prescribes the acceptable population of microorganisms that are included and live in ballast water discharged from a ship with differentiation based on the minimum size of the microorganisms, and for example, it prescribes that the acceptable population of microorganisms having a minimum size of 50 µm or more (hereinafter, referred to as "L size organisms") is $10/m^3$ or less, and that of microorganisms having a minimum size of 10 µm or more and less than 50 µm (hereinafter, referred to as "S size organisms") is 10/mL or less.

As a technique for confirming whether the above Discharge Standards are satisfied when the ballast water is discharged, examination apparatuses for microorganisms have been heretofore known, such as an examination apparatus described in Patent Literature 1, in which seawater pumped up by a water pump is passed through flow cells and subjected to image measurement, and an examination apparatus described in Patent Literature 2, in which seawater pumped up by a water pump is passed through a unit of filters having different apertures, followed by allowing microorganisms on the filters to emit light and counting the number of the microorganism.

The examination apparatus for microorganisms described in Patent Literature 1 includes a staining portion that, while allowing a liquid analyte to flow, stains organisms having living cells present in the analyte; a concentrating portion that, while allowing the stained analyte to flow, performs concentrating so that the concentration of the organisms is increased; an individual measurement portion that acquires image information on individuals including the organisms in the concentrated analyte; and a controlling means that performs measurement of the organisms based on the image information on the individuals output by the individual measurement portion.

Thus, the examination apparatus can perform a step of staining the organisms in the liquid of the analyte, a step of concentrating the organisms in the liquid, a step of acquiring the information on the organisms in the liquid, and the like in a flow system, and therefore has the following advantages as compared with a technique in which the each steps are performed in a batch system: a waiting time until the analyte after completion of one step partially proceeds to the next step can be significantly reduced or can be eliminated, and stable information on the life and death of the organisms can be acquired in the view that deterioration in the state of staining during the waiting time is prevented.

The examination apparatus for microorganisms described in Patent Literature 1, however, allows the seawater pumped by the water pump to sequentially pass through the each steps, and therefore has the problems of being a large-scale apparatus and being high in production cost. Further, although the examination apparatus allows the seawater to sequentially pass through the each steps for a reduction in waiting time, it has the problem of taking at least several hours for the completion of measurement.

In addition, in the examination apparatus for microorganisms described in Patent Literature 2, there are a step of passing the seawater through the unit of filters which is formed by arranging of three filters each having a different aperture in series; a step of allowing the microorganisms trapped in the filters and living therein to conduct any of color development, light emission and fluorescence emission; and a step of detecting any of color development, light emission and fluorescence emission to count the number of the microorganisms in the ballast water or seawater by image analysis.

Thus, the following advantage is provided: capturing the microorganisms by the stepwise size can be realized and, as a result, whether the standard of the acceptable residue for each size is satisfied can be rapidly measured.

The examination apparatus for microorganisms described in Patent Literature 2, however, also allows the seawater pumped by the water pump to sequentially pass through the each steps, and has the problems of being a large-scale apparatus and being high in production cost, as in the examination apparatus for microorganisms described in Patent Literature 1.

In view of the above problems, the present applicant has proposed, in Patent Literature 3, a method for examining microorganisms, in which a batch type measurement cell can be utilized to thereby measure the number of microorganisms in ballast water simply in a short time at a high accuracy.

The method for examining microorganisms proposed by the present applicant includes a stirring and mixing step of stirring and mixing a sample solution obtained by adding a fluorescence staining reagent to a sample in a batch type sample container; an excitation step of irradiating a surface to be irradiated of the sample container with excitation light while stirring the sample solution; a light reception step of counting the number of fluorescence emissions of microorganisms that emit fluorescence by the excitation light; and an estimation step of the number of microorganisms, which is a step of calculating the amount of microorganisms included in the sample in the sample container from the number of the fluorescence emissions detected in the light reception step.

Therefore, the method has the following actions and effects: microorganisms can brightly emit light in an extremely short time, by which the amount the microorganisms in the ballast water can be measured simply in a short time; and the thickness portion of the fluorescence emission is reduced, which results in that the difference in the amount of light between the background and the fluorescence emission of microorganisms become extremely clear to enhance the detection accuracy of the fluorescence emission of microorganisms.

For example, as illustrated in FIG. 6, the detection principle of microorganisms described above is as follows: microorganisms such as planktons subjected to fluorescence staining can be detected as electric signals in a photomultiplier tube, and a background component, for example, of a voltage of about 0.9 V continuously detected can be compared with a fluorescence intensity when living planktons pass to distinguish the peak height of the fluorescence intensity when the planktons pass, namely, the height of the voltage from the background component. The background component here is based on the fluorescence of sample water by itself, namely, intrinsic fluorescence or the fluorescence due to spontaneous decomposition of a staining agent in sample water.

In the above proposition, however, as the background component is larger, a noise component tends to be also larger, and as a result, a problem is that a larger background component causes a reduction in the S/N ratio to affect the detection accuracy.

CITATION LIST

Patent Literature

Patent Literature 1 Japanese Patent Laid-Open No. 2009-85898
Patent Literature 2 Japanese Patent Laid-Open No. 2007-135582
Patent Literature 3 Japanese Patent Laid-Open No. 2014-042463

SUMMARY

Technical Problem

In view of the above problems, a technical object of the present invention is to provide a method for detecting microorganisms, in which fluorescence emission of the background component can be reduced to result in an enhancement in detection accuracy.

Solution to Problem

The method for examining microorganisms according to the present invention is a method for measuring an amount of microorganisms in a sample, the measurement of an amount of microorganisms in the sample including a sampling preparation step of stirring and mixing a sample and a fluorescence staining reagent to prepare a sampling, and a calculation step of an amount of microorganisms, which is a step of calculating an amount of microorganisms from the number of light emissions in fluorescence emission obtained by irradiation of the sampling with excitation light of a specific wavelength, wherein the sampling preparation step includes a fluorescence staining step of stirring and mixing certain amounts of the sample and the fluorescence staining reagent, a still standing step of leaving a solution after the fluorescence staining step to still stand for a certain time, and a dilution step of diluting a solution after the still standing step with a liquid that emits no fluorescence.

In the fluorescence staining step, 1 to 10% by volume of the sample based on the total volume of a sample container may be loaded into the sample container together with 1% by volume of the fluorescence staining reagent based on the volume of the sample may be loaded into the sample container, and the sample and the fluorescence staining reagent may be stirred and mixed. Furthermore, FDA may be used as the fluorescence staining reagent and added so that the concentration thereof in the sample before dilution is 0.01 mM.

The method for examining microorganisms of the present invention is a method for measuring an amount of microorganisms in a sample, the measurement of an amount of microorganisms in the sample including a sampling preparation step of stirring and mixing a sample and a fluorescence staining reagent to prepare a sampling, and a calculation step of an amount of microorganisms, which is a step of calculating an amount of microorganisms from the number of light emissions in fluorescence emission obtained by irradiation of the sampling with excitation light of a specific wavelength, wherein the sampling preparation step includes a fluorescence staining step of stirring and mixing certain amounts of the sample and the fluorescence staining reagent, a still standing step of leaving a solution after the fluorescence staining step to still stand for a certain time, and a pH adjustment step of adding a pH adjuster to a solution after the still standing step. In the pH adjustment step, when a pH of the solution in the fluorescence staining step is 8.0, the pH adjuster may be added so that the pH is 6.0 in the pH adjustment step.

Advantageous Effects of the Invention

According to the method for examining microorganisms of the present invention, a small amount of the sample is first stirred and mixed with the fluorescence staining reagent in the fluorescence staining step, and the resulting solution is then left to still stand for a certain time in the still standing step and is further diluted with the liquid that emits no fluorescence in the dilution step. Thus, microorganisms included in a small amount of the sample can be stirred and mixed with the fluorescence staining reagent and extremely clearly stained without any plaques in the fluorescence staining step. Therefore, staining activity of the fluorescence staining reagent can be no longer exhibited when the dilution liquid is added in the dilution step, and fluorescence emission of the background component can be reduced to increase the S/N ratio, resulting in a remarkable enhancement in detection accuracy in the calculation step of the amount of microorganisms as the final step. In the fluorescence staining step, 1 to 10% by volume of the sample based on the total volume of the sample container can be loaded into the sample container together with 1% by volume of the fluorescence staining reagent based on the volume of the sample, and the sample and the fluorescence staining reagent can be stirred and mixed, thereby resulting in a further enhancement in detection accuracy. Furthermore, it is effective that FDA be used as the fluorescence staining reagent and added so that the concentration thereof in the sample before dilution is 0.01 mM.

In the method for examining microorganisms of the present invention, the sampling preparation step includes the fluorescence staining step of stirring and mixing certain amounts of the sample and the fluorescence staining reagent, the still standing step of leaving the solution after the fluorescence staining step to still stand for a certain time, and the pH adjustment step of adding the pH adjuster to the solution after the still standing step. For example, when the pH of the sample is weakly alkaline in the fluorescence staining step, microorganisms included in the sample are extremely clearly stained without any plaques upon stirring and mixing with the fluorescence staining reagent. Therefore, when the pH of the sample is adjusted to weak acidity by adding of the pH adjuster in the pH adjustment step, staining activity of the fluorescence staining reagent can be no longer exhibited, and fluorescence emission of the background component can be reduced to increase the S/N ratio, resulting in a remarkable enhancement in detection accuracy in the calculation step of the amount of microorganisms as the final step. In the pH adjustment step, when the pH of the solution in the fluorescence staining step is 8.0, the pH adjuster can be added so that the pH becomes 6.0 in the pH adjustment step, thereby resulting in a further enhancement in detection accuracy.

BRIEF DESCRIPTION OF THE DRAWINGS

FIG. 5 is a voltage waveform diagram illustrating one example of a background component diluted.

DETAILED DESCRIPTION

Figure 1:
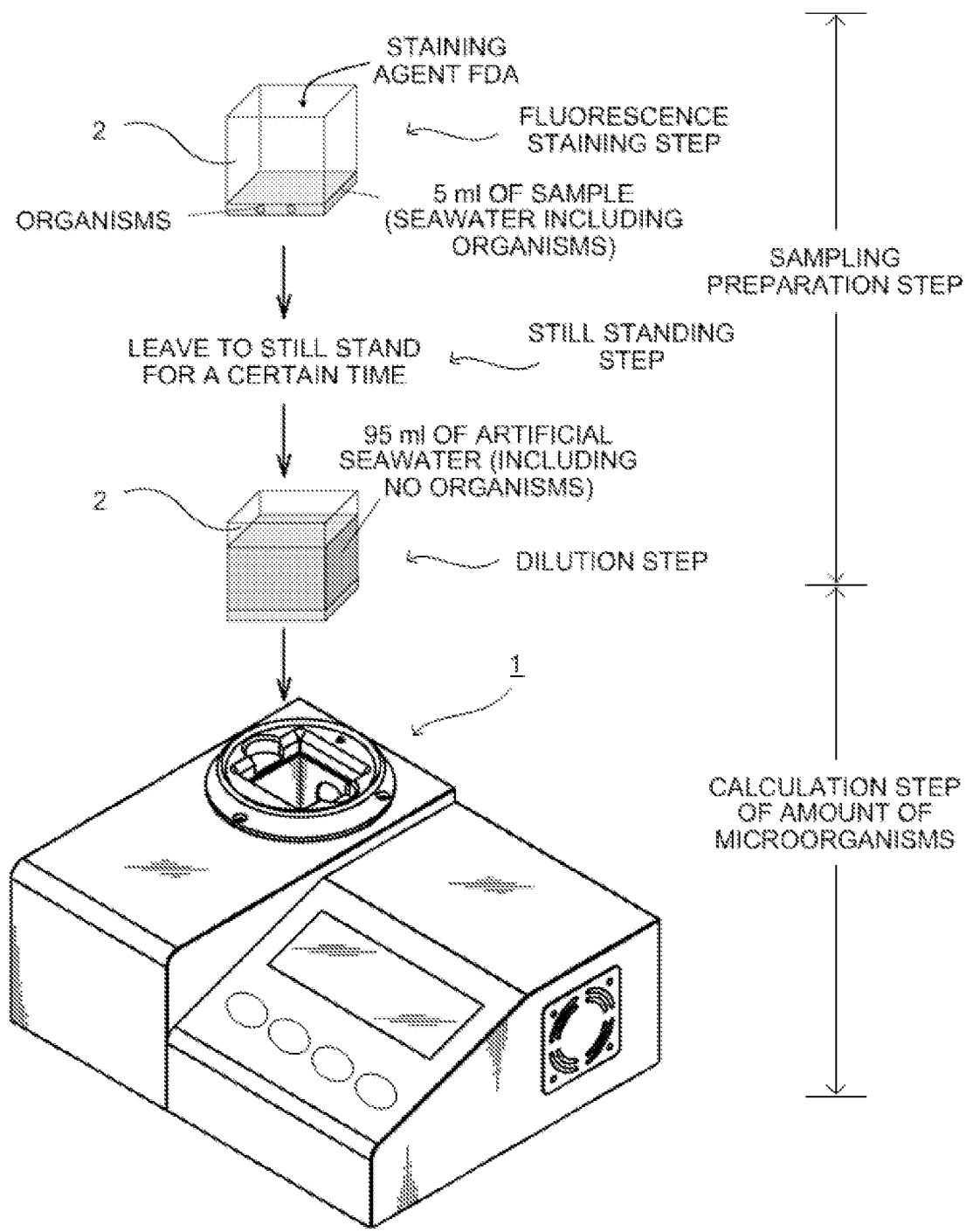
FIG. 1 is a schematic process diagram of a method for examining microorganisms according to the first embodiment.
Figure 2:
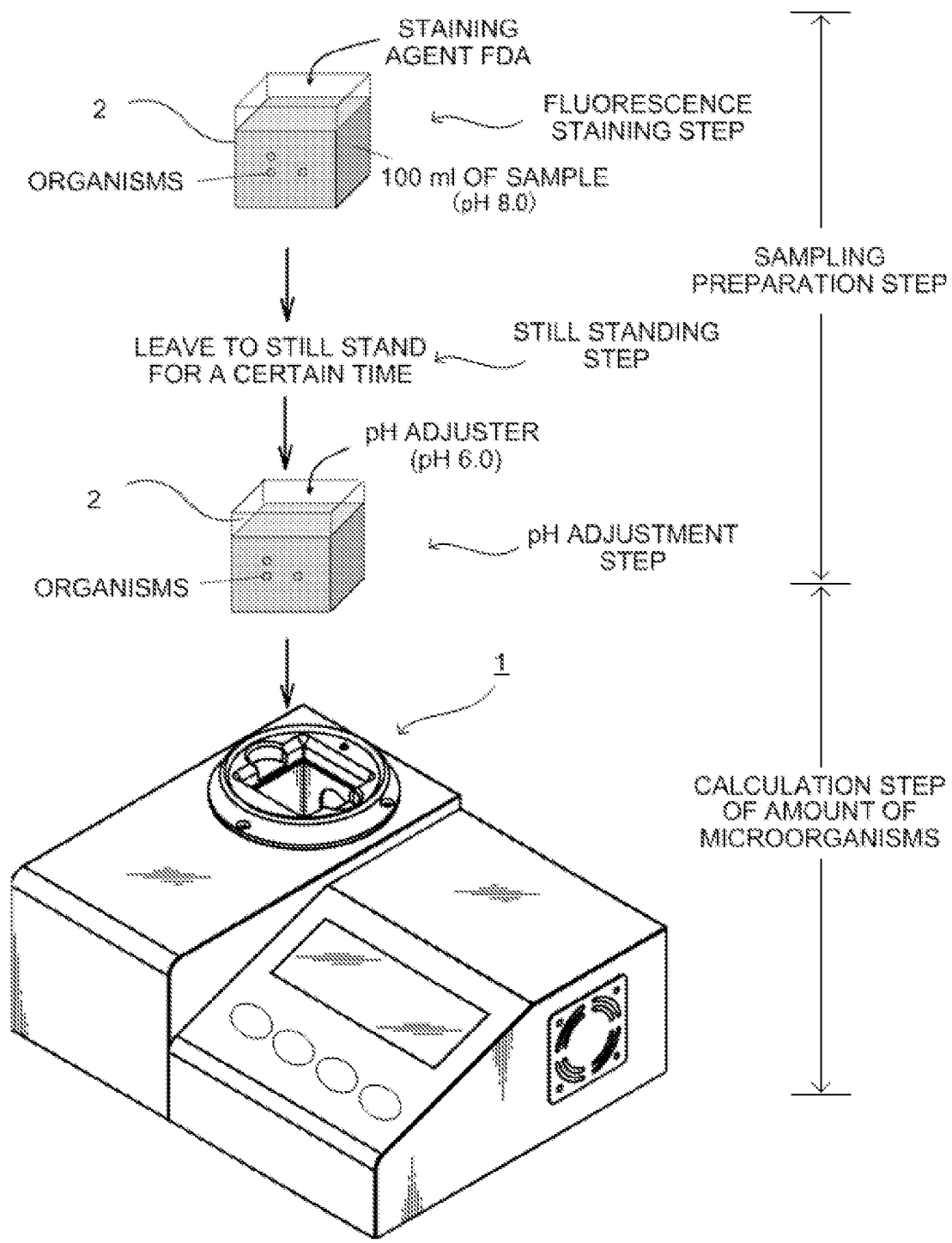
FIG. 2 is a schematic process diagram of a method for examining microorganisms according to the second embodiment.

FIG. 1 is a schematic process diagram of a method for examining microorganisms according to a first embodiment, and FIG. 2 is a schematic process diagram of a method for examining microorganisms according to a second embodiment.

As illustrated in FIG. 1 and FIG. 2, the method for examining microorganisms includes a sampling preparation step of collecting ballast water as a sample, and stirring and mixing the sample and a fluorescence staining reagent to prepare a sampling, and a calculation step of the amount of microorganisms, which is a step using an examination apparatus 1 for microorganisms and which is a step of calculating the amount of microorganisms from the number of light emissions in fluorescence emission obtained by irradiation of the sampling prepared in the sampling preparation step with excitation light of a specific wavelength.

In the first embodiment of the present invention, the sampling preparation step includes a fluorescence staining step of stirring and mixing certain amounts of the sample and the fluorescence staining reagent, a still standing step of leaving the solution after the fluorescence staining step to still stand for a certain time, and a dilution step of diluting the solution after the still standing step with a liquid that emits no fluorescence.

In the second embodiment, the sampling preparation step includes a fluorescence staining step of stirring and mixing certain amounts of the sample and the fluorescence staining reagent, a still standing step of leaving the solution after the fluorescence staining step to still stand for a certain time, and a pH adjustment step of adding a pH adjuster to the solution after the still standing step.

The sampling preparation step of the first embodiment will be described with reference to FIG. 1. An operator provides, for example, a 100-ml sample container 2 formed from a transparent material that penetrates light, such as a glass, quartz or an acrylic resin, in advance. Then, a sample is collected in the sample container 2 and a fluorescence staining reagent or the like is added thereto for preparation. Thereafter the sample container 2 is accommodated in the examination apparatus 1 for microorganisms, and the amount of microorganisms is calculated. Hereinafter, "ml" represents milliliter.

In measurement of the amount of microorganisms, it is desirable to concentrate a large amount of ballast water in a certain amount in advance. Then, the operator collects the ballast water concentrated in a certain amount as the sample by use of a pipette or the like, and loads 1 to 10% by volume of the sample based on the total volume of the sample container 2 into the sample container 2. For example, when the total volume of the sample container is 100 ml, the amount to be loaded into the sample container 2 is in the range of 1 to 10 ml, and is more preferably 5 ml.

Next, the fluorescence staining reagent is added into the sample container 2. As the fluorescence staining reagent, Calcein AM (Calcein-AM, produced by Promocell GmbH, Germany) or FDA, e.g., Fluorescein diacetate, which are commonly known, or the like can be used. While Calcein AM tends to easily stain phytoplanktons, FDA tends to easily stain zooplanktons. In the present invention, FDA is preferably used as the staining reagent. When the concentration of FDA is here 1 mM, 1% by volume of the staining reagent based on the volume of the sample is preferably loaded into the sample container 2. That is, when 1 ml of the sample is collected, 0.01 ml, namely, 10 µL of FDA in a concentration of 1 mM may be added; when 5 ml of the sample is collected, 0.05 ml, namely, 50 µL of FDA in a concentration of 1 mM may be added; and when 10 ml of the sample is collected, 0.1 ml, namely, 100 µL of FDA in a concentration of 1 mM may be added. Thereafter, the operator stirs and mixes the sample solution in the sample container 2 by a stirring means such as a rotor. The foregoing describes the fluorescence staining step in FIG. 1.

Next, in the still standing step in FIG. 1, the operator leaves the sample container 2 after the fluorescence staining step, for a certain time. With respect to the conditions here, the sample container 2 is preferably left to still stand under an environment of 20° C. for about 30 minutes.

Furthermore, in the dilution step in FIG. 1, the operator performs dilution by use of a liquid that emits no fluorescence, in the sample container 2 after the still standing step. In the dilution, for example, artificial seawater generating a low background noise, namely, emitting no fluorescence may be used, and the amount to be loaded into the sample container 2 as the amount of dilution may be in the range of 90 ml to 99 ml depending on the amount of the sample to be collected. Herein, the liquid that emits no fluorescence is not limited to artificial seawater, and for example, a sample including organisms not stained, before the fluorescence staining reagent is added thereto, can be applied as the liquid that emits no fluorescence. Thus, the following advantage is provided: the liquid that emits no fluorescence, such as artificial seawater, is not required to be separately provided and prepared.

As described above, a small amount of the sample is first stirred and mixed with the fluorescence staining reagent, the resulting solution is then left to still stand for a certain time, and the solution left to still stand is further diluted with the liquid that emits no fluorescence. Thus, microorganisms included in a small amount of the sample can be stirred and mixed with the fluorescence staining reagent and extremely clearly stained without any plaques, and staining activity of the fluorescence staining reagent can be no longer exhibited in adding of the dilution liquid, which results in that fluorescence emission of the background component can be reduced.

Next, the sampling preparation step of the second embodiment will be described with reference to FIG. 2. As in the above embodiment, an operator prepares a 100-ml sample container 2 in advance. Then, the operator collects ballast water concentrated in a certain amount as the sample by use of a pipette or the like, and loads the sample in an amount of the total volume of the sample container 2 into the sample container 2. For example, when the total volume of the sample container is 100 ml, 100 ml of the sample is loaded into the sample container 2. Then, FDA may be used as the fluorescence staining reagent, and also 1 ml, namely, 1000 μL of FDA in a concentration of 1 mM may be added to 100 ml of the sample. Thereafter, the operator mixes and stirs the sample solution in the sample container 2 by use of a stirring means such as a rotor. The foregoing describes the fluorescence staining step in FIG. 2. The pH of the solution here is about 8.0 which is weakly alkaline.

Then, as the still standing step in FIG. 2, the operator leaves the sample container 2 after the fluorescence staining step, for a certain time. With respect to the conditions here, the sample container 2 is preferably left to still stand under an environment of 20° C. for about 30 minutes.

Next, in the pH adjustment step in FIG. 2, the operator adds a pH adjuster to the sample container 2 after the still standing step to adjust the pH of the solution to about 6.0, which is weakly acidic. For example, an MES buffer may be used as the pH adjuster, and the concentration of the pH adjuster and the amount thereof to be loaded are appropriately modulated so that the pH shifts from 8.0 to 6.0.

As described above, the sample is first stirred and mixed with the fluorescence staining reagent, the resulting solution is then left to still stand for a certain time, and the pH adjuster is further added to the solution left to still stand so as to adjust the pH. Thus, in the initial fluorescence staining step, the pH is weakly alkaline, and microorganisms included in the sample are stirred and mixed with the fluorescence staining reagent and extremely clearly stained without any plaques. In addition, in the last pH adjustment step, the pH adjuster is added to thereby allow the pH to shift to weakly acidic, and staining activity of the fluorescence staining reagent is no longer exhibited, which results in that fluorescence emission of the background component can be reduced.

The sampling preparation step of each of the first embodiment in FIG. 1 and the second embodiment in FIG. 2 is followed by the calculation step of the amount of microorganisms below.

Figure 3:
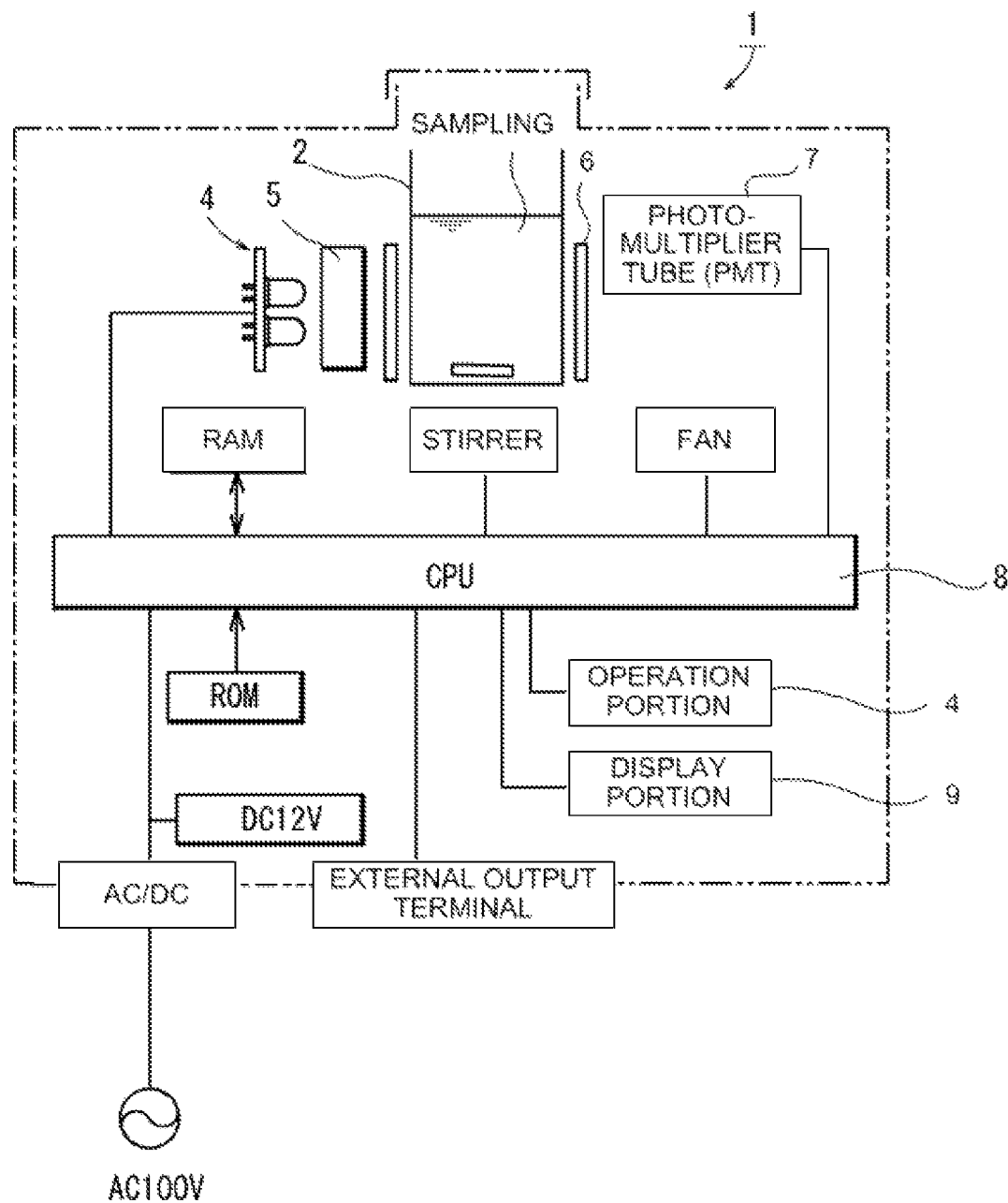
FIG. 3 is a schematic view of an examination apparatus to be applied to the method for examining microorganisms.

FIG. 3 is a schematic view of an examination apparatus to be applied to the method for examining microorganisms. The principle of such an examination apparatus 1 is as follows. A sample container 2 is installed to the examination apparatus 1, a measurement starting button of an operation portion 3 is pressed to thereby turn on an LED light source 4 after a predetermined time, and the sample container 2 is irradiated with light that penetrates a band pass filter for excitation light 5. Here, the sample container 2 is irradiated with, for example, light of wavelengths of 450 nm to 490 nm as wavelength properties to allow an analyte in the sample container 2, namely, microorganisms to emit fluorescence.

Then, the fluorescence penetrates a band pass filter for fluorescence 6, and is detected by a photomultiplier tube (PMT) 7.

The photomultiplier tube (PMT) 7 can convert light energy to electric energy by use of the photoelectric effect, and can also have a current amplification function added, to detect fluorescence emission at a high sensitivity. The electric signal detected is sent to a CPU board 8, and the number of received light waveforms of a certain threshold or more is counted.

Furthermore, in the CPU board 8, the number of microorganisms present in 100 ml of water in the sample container 5 is estimated from the number counted based on the received light waveforms, and whether the number of microorganisms satisfies the effluent standard is displayed on a display portion 9.

Hereinafter, the results of the above first embodiment are verified.

Whether the background is reduced by dilution to result in a reduction in noise to enhance the S/N ratio, as in the first embodiment described above, has been verified.

Figure 4:
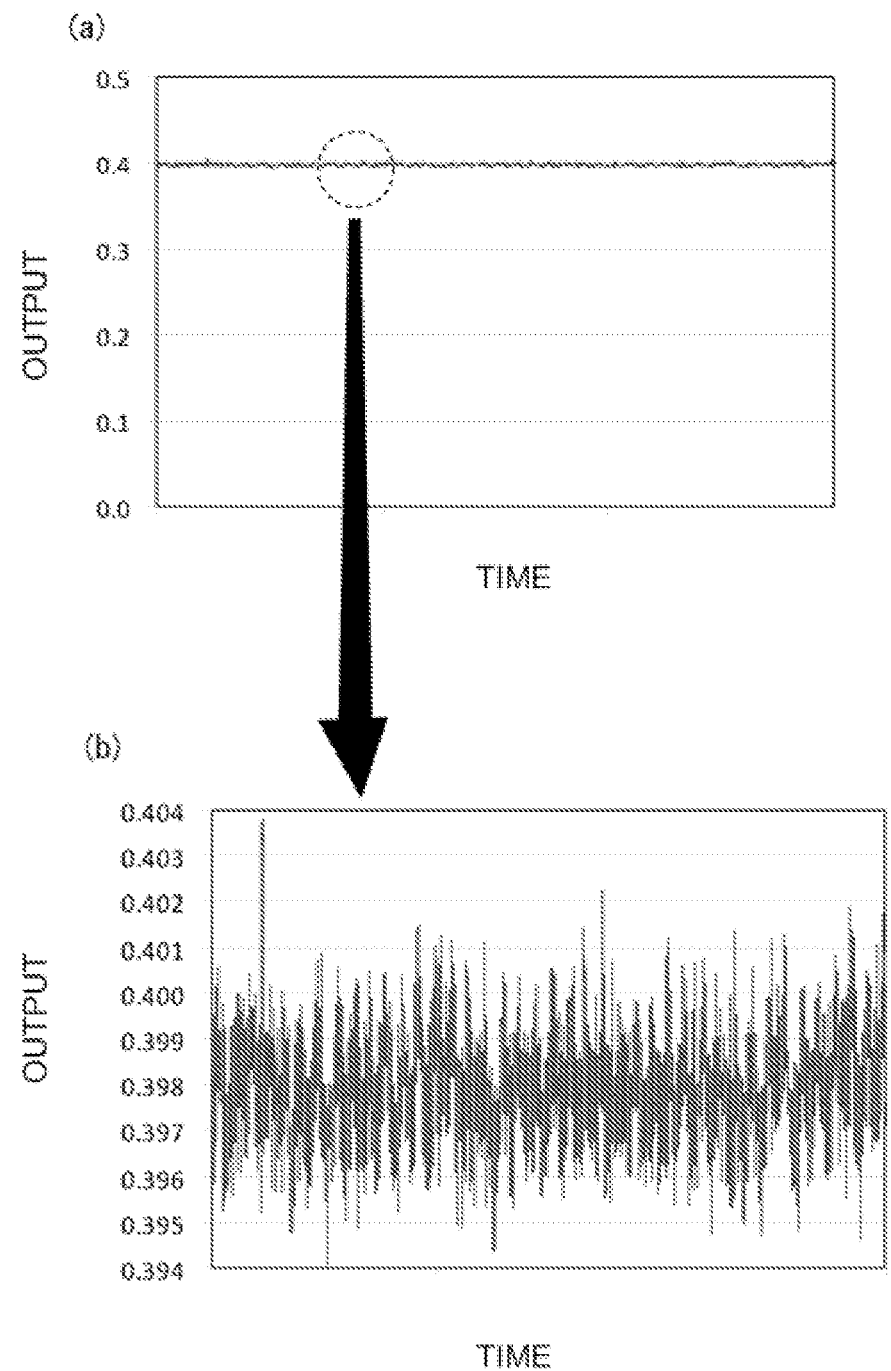
FIG. 4 is a voltage waveform diagram illustrating one example of a background component not diluted.
Figure 6:
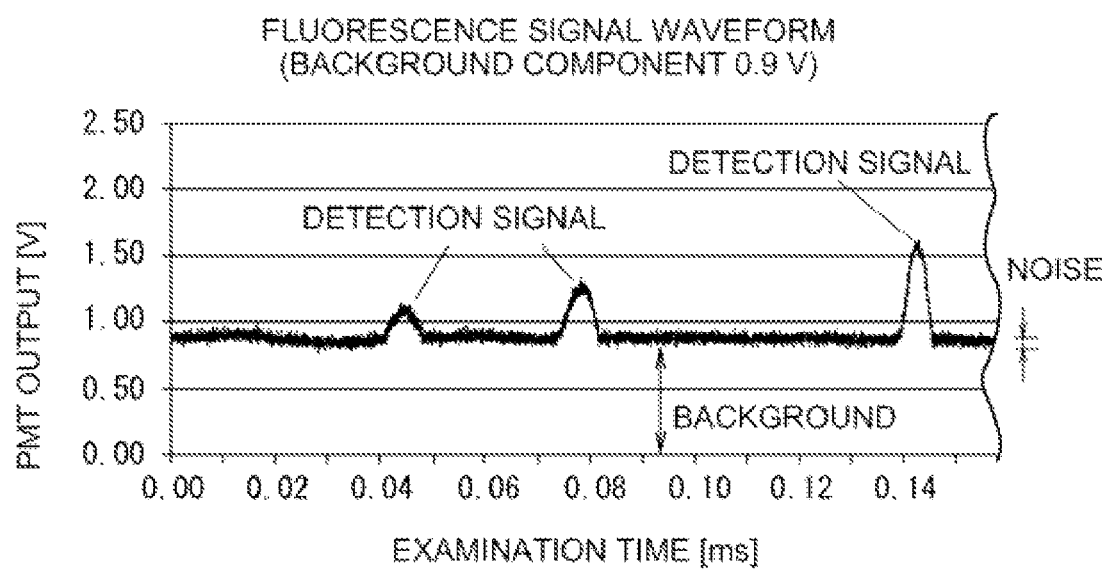
FIG. 6 is a diagram illustrating voltage waveform for a comparison of a conventional background component and the fluorescence intensity when living planktons pass.

As one example not diluted, 5 ml of seawater including organisms, as a sample, 95 ml of artificial seawater including no organisms, and 1 ml of FDA in a concentration of 1 mM were loaded into a sample container 2 having a total volume of 100 ml, and were stirred and mixed. The sample container 2 was left to still stand for a certain time, specifically, left to still stand under an environment of 20° C. for about 30 minutes, and subjected to measurement by an examination apparatus 1. The background component here is illustrated in FIG. 4(a). In addition, an enlarged diagram is illustrated in FIG. 4(b). Here, the voltage of the background component was 0.3977 V, the signal voltage S was 0.006118 V, the noise voltage N was 0.001157 V, and the S/N ratio was 5.2878.

As one example diluted, a sample was adjusted according to the technique in paragraphs 0025 to 0030 described above, and subjected to measurement by the examination apparatus 1. The background component here is illustrated in FIG. 5(a). In addition, an enlarged diagram is illustrated in FIG. 5(b). Here, the voltage of the background component was 0.03977 V, the signal voltage S was 0.006354 V, the noise voltage N was 0.000479 V, and the S/N ratio was 13.2651.

In comparison of the example not diluted, with the example diluted, the voltage of the background component was reduced to about 1/20 and the S/N ratio was increased about 2.5 times.

According to the present embodiments, as described above, a small amount of the sample is stirred and mixed with the fluorescence staining reagent in the fluorescence staining step, the resulting solution is then left to still stand for a certain time in the still standing step, and the solution is further diluted with the liquid that emits no fluorescence in the dilution step. Therefore, microorganisms included in a small amount of the sample can be stirred and mixed with the fluorescence staining reagent and extremely clearly stained without any plaques in the fluorescence staining step, staining activity of the fluorescence staining reagent can be no longer exhibited in adding of the dilution liquid in the dilution step. Thus, fluorescence emission of the background component can be reduced to increase the S/N ratio, resulting in a remarkable enhancement in detection accuracy in the calculation step of the amount of microorganisms as the final step.

In addition, in the case where the sampling preparation step includes the fluorescence staining step of stirring and mixing certain amounts of the sample and the fluorescence staining reagent, the still standing step of leaving the solution after the fluorescence staining step to still stand for a certain time, and the pH adjustment step of adding the pH adjuster to the solution after the still standing step, when the pH of the sample is weakly alkaline in the fluorescence staining step, microorganisms included in the sample are extremely clearly stained without any plaques upon stirring and mixing with the fluorescence staining reagent. Therefore, when the pH of the sample is adjusted to weak acidity by adding of the pH adjuster in the pH adjustment step, staining activity of the fluorescence staining reagent can be no longer exhibited, and fluorescence emission of the background component can be reduced to increase the S/N ratio, resulting in a remarkable enhancement in detection accuracy in the calculation step of the amount of microorganisms as the final step.

INDUSTRIAL APPLICABILITY

The present invention can be applied to, for example, a method for detecting microorganisms, in which fluorescence emission of the background component can be reduced to result in an enhancement in detection accuracy.

LIST OF REFERENCE NUMBERS 1 examination apparatus
2 sample container
3 operation portion
4 LED light source
5 band pass filter for excitation light
6 band pass filter for fluorescence
7 photomultiplier tube (PMT)
8 CPU board
9 display portion

What is claimed is:

1. A method for measuring an amount of microorganisms in a seawater sample, comprising:
   i. concentrating a sample of seawater containing microorganisms and placing the concentrated sample in a transparent sample container;
   ii. stirring and mixing an amount the concentrated sample with an amount of a fluorescence staining reagent to form a mixed solution;
   iii. letting the mixed solution still-stand for a suitable period of time then diluting the mixed solution with a liquid that emits no fluorescence to form a test sample,
   iv. irradiating the test sample with an excitation light of a specific wavelength, and
   v. calculating an amount of microorganisms in the irradiated test sample based on the number of light emissions in fluorescence emission,
      wherein the amount of the concentrated sample is from 1% (v/v) to 10% (v/v) and the amount of the fluorescence staining reagent is 1% (v/v), by volume of the sample container,
      wherein the fluorescence staining reagent comprises fluorescein diacetate (FDA), and
      wherein the concentration of the FDA in the mixed solution, before dilution, is 0.01 mM.

2. A method for measuring an amount of microorganisms in a seawater sample, comprising:
   i. concentrating a sample of seawater containing microorganisms and placing the concentrated sample in a transparent sample container;
   ii. stirring and mixing an amount the concentrated sample with an amount of a fluorescence staining reagent to form a mixed solution;
   iii. letting the mixed solution still-stand for a suitable period of time then diluting the mixed solution with a liquid that emits no fluorescence to form a test sample,
   iv. irradiating the test sample with an excitation light of a specific wavelength, and
   v. calculating an amount of microorganisms in the irradiated test sample based on the number of light emissions in fluorescence emission,
      wherein the amount of the concentrated sample is from 1% (v/v) to 10% (v/v) and the amount of the fluorescence staining reagent is 1% (v/v), by volume of the sample container,
      wherein the fluorescence staining reagent comprises fluorescein diacetate (FDA),
      wherein the concentration of the FDA in the mixed solution, before dilution, is 0.01 mM, and
      wherein the method further comprises adjusting the pH of the mixed solution to 6.0 following step iii.

* * * * *